US012797532B2

(12) United States Patent
Kuga et al.

(10) Patent No.: US 12,797,532 B2
(45) Date of Patent: Nov. 17, 2026

(54) NEUTROPHIL DEPLETING MATERIAL AND METHOD OF PRODUCING NEUTROPHIL DEPLETING MATERIAL

(71) Applicant: Toray Industries, Inc., Tokyo (JP)

(72) Inventors: Chisa Kuga, Otsu (JP); Megumi Nakanishi, Otsu (JP); Hiroshi Takahashi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 240 days.

(21) Appl. No.: 18/834,550

(22) PCT Filed: Feb. 28, 2023

(86) PCT No.: PCT/JP2023/007307
§ 371 (c)(1),
(2) Date: Jul. 30, 2024

(87) PCT Pub. No.: WO2023/167184
PCT Pub. Date: Sep. 7, 2023

(65) Prior Publication Data

US 2025/0114508 A1 Apr. 10, 2025

(30) Foreign Application Priority Data

Mar. 3, 2022 (JP) ................................ 2022-032411

(51) Int. Cl.
*D06M 13/325* (2006.01)
*A61M 1/36* (2006.01)
(Continued)

(52) U.S. Cl.
CPC ....... *A61M 1/3633* (2013.01); *B01D 39/1623* (2013.01); *D06M 13/325* (2013.01);
(Continued)

(58) Field of Classification Search
CPC ........ A61M 1/3633; A61M 2202/0439; B01D 39/1623; D06M 13/325
See application file for complete search history.

(56) References Cited

U.S. PATENT DOCUMENTS 6,878,269 B2 * 4/2005 Nanko ................ B01J 20/3219
210/287
10,888,840 B2 * 1/2021 Tomita .............. B01J 20/28023
(Continued)

FOREIGN PATENT DOCUMENTS

JP 2008-80114 A 4/2008
JP 2019-136499 A 8/2019
(Continued)

OTHER PUBLICATIONS

International Search Report dated May 9, 2023, of counterpart International Application No. PCT/JP2023/007307 along with an English translation.

(Continued)

*Primary Examiner* — Guy K Townsend
(74) *Attorney, Agent, or Firm* — DLA Piper LLP (US)

(57) ABSTRACT

A material removes neutrophils while suppressing removal of platelets, the material being a knitted fabric or a woven fabric including a fiber having a fiber diameter of 10 to 60 μm, wherein the knitted fabric or the woven fabric has a thickness of 0.10 to 0.40 mm and a porosity of 10 to 30%.

9 Claims, 1 Drawing Sheet

(51) Int. Cl.
*B01D 39/16* (2006.01)
*D06M 101/20* (2006.01)

(52) U.S. Cl.
CPC ................ *A61M 2202/0439* (2013.01); *B01D 2239/1233* (2013.01); *D06M 2101/20* (2013.01)

(56) References Cited

U.S. PATENT DOCUMENTS

| | | | | |
|---|---|---|---|---|
| 2004/0104165 | A1* | 6/2004 | Oishi | A61M 1/3633 210/507 |
| 2008/0000830 | A1* | 1/2008 | Mabuchi | B01D 67/009 210/500.23 |
| 2009/0275874 | A1* | 11/2009 | Shimagaki | B01J 20/265 604/6.03 |
| 2010/0025335 | A1* | 2/2010 | Shimaki | A61M 1/3679 210/690 |
| 2011/0031191 | A1* | 2/2011 | Fukuda | B01D 39/083 210/491 |
| 2019/0184371 | A1* | 6/2019 | Kanda | B01J 20/28016 |
| 2021/0213421 | A1* | 7/2021 | Kanda | D01F 8/06 |
| 2022/0362742 | A1* | 11/2022 | Yamashita | B01J 20/3219 |
| 2024/0116004 | A1* | 4/2024 | Yamashita | B01D 71/421 |
| 2025/0114508 | A1* | 4/2025 | Kuga | D06M 16/00 |

FOREIGN PATENT DOCUMENTS

| | | | |
|---|---|---|---|
| JP | 2021-145918 | A | 9/2021 |
| WO | 2015/194668 | A1 | 12/2015 |
| WO | 2018/047929 | A1 | 3/2018 |
| WO | 2021/0661521 | A1 | 4/2021 |

OTHER PUBLICATIONS

Handa, M., "Platelet preparations (indications and usage of blood preparations)," *Japanese Journal of Thrombosis and Hemostasis*, 2009, vol. 20, No. 5, pp. 495-497, along with an English abstract.

Yoshimura, N. et al. "Correlation of the Pressure Difference with the Removal Rates of Peripheral Leukocyte and Platelets during Leukocytapheresis," *Japanese Journal of Apheresis*, 2008, vol. 27, No. 1, pp. 56-60, along with an English abstract.

* cited by examiner

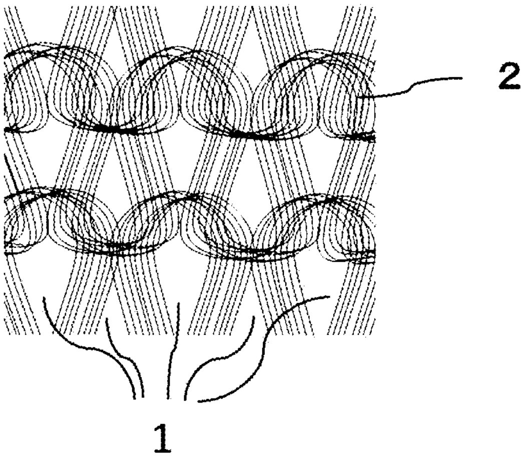
2
1

NEUTROPHIL DEPLETING MATERIAL AND METHOD OF PRODUCING NEUTROPHIL DEPLETING MATERIAL

CROSS-REFERENCE TO RELATED APPLICATIONS

This application is a US national stage filing under 35 U.S.C. § 371 of International Application No. PCT/JP2023/007307, filed Feb. 28, 2023, which claims priority to Japanese Patent Application No. 2022-032411, filed Mar. 3, 2022, each of which is incorporated herein by reference in its entirety.

TECHNICAL FIELD

This disclosure relates to a material for removing neutrophils, and a method of producing the material for removing neutrophils.

BACKGROUND

Neutrophils account for about 60% of peripheral blood leukocytes, and play a central role in the protection against infection, through phagocytosis, or release of inflammatory cytokines and the like. On the other hand, hyperactivation of neutrophils may lead to damaging of own tissues to cause organ dysfunction.

To remove inflammatory cytokines, or activated leukocytes that serve as a source of those cytokines, extracorporeal circulation therapy has so far been employed as a therapeutic method for inflammatory diseases such as acute respiratory distress syndrome (ARDS), acute lung injury (ALI), systemic lupus erythematosus, rheumatoid arthritis, multiple sclerosis, ulcerative colitis, and Crohn's disease.

In general, removal of platelets from blood of a patient during extracorporeal circulation therapy leads to a decrease in the hemostatic function of the patient, and hence an increase in the risk of bleeding during and after the treatment. Further, in cases where platelets adhere to a material such as a material for removing neutrophils used in the extracorporeal circulation therapy, clogging of the material for removing neutrophils occurs to increase the pressure during the circulation, so that continuation of the treatment becomes impossible. Therefore, the platelet removal rate by the material for removing neutrophils used in extracorporeal circulation therapy is preferably low.

The platelet count in peripheral blood of an adult is 130,000 to 370,000/μL, and the critical platelet count at which the bleeding time, which represents the primary hemostatic function of platelets, is elongated is 100,000/μL (Makoto Handa, "Blood Products", Japanese Journal of Thrombosis and Hemostasis, 2009, Vol. 20, No. 5, p. 495-497). Further, it has been reported that, in leukocytapheresis (LCAP), the platelet removal rate was 36.8% when a pressure increase occurred, while the platelet removal rate was 21.8% when no pressure increase occurred (Noriko Yoshimura et al. "Correlation of the Pressure Difference with the Removal Rates of Peripheral Leukocyte and Platelets during Leukocytapheresis", Japanese Journal of Apheresis, 2008, Vol. 27, No. 1, p. 56-60). It is thus known that, with a platelet removal rate of not more than 22%, the platelet count can be maintained within a range that allows normal hemostatic function, and the circulation can be carried out for a long time while avoiding the pressure increase.

As a material for removing neutrophils that is applicable to extracorporeal circulation therapy, WO 2018/047929 discloses a material for blood purification capable of removing an activated granulocyte-activated platelet complex, wherein the material has specific contents of amide groups and amino groups. WO 2018/047929 discloses that a preferred porosity for the suppression of the pressure increase is 0.1 to 30.0%, especially preferably 7.0 to 15.0%.

JP 2019-136499 A discloses a material for removing an activated granulocyte-activated platelet complex, wherein the material has a specific content of amide groups.

WO 2015/194668 discloses a column for removing neutrophils, comprising a fibrous carrier having a specific surface area and a specific average fiber diameter, wherein the column is capable of controlling the platelet count within a range in which the homeostatic function can be maintained.

JP 2008-80114 A discloses an adsorption carrier for removal of cells in blood, the adsorption carrier comprising a combination of fibers having a plurality of fiber diameters.

However, although WO 2018/047929 discloses that the platelet adsorption rate can be suppressed by setting the porosity within a preferred range and introducing phenyl groups, the platelet adhesion rate in the Examples was not less than 72%. This is a very high rate, and hence the suppression was insufficient for maintaining the platelet count within a range that allows normal hemostatic function. Moreover, there is neither disclosure nor suggestion on an idea about the thickness of the material for removing neutrophils for the suppression of the platelet removal.

JP 2019-136499 A discloses that the smaller the amino group content or the sulfonic acid group content, the lower the platelet removal rate. However, there is neither disclosure nor suggestion on an idea about the thickness or the porosity of the material for removing neutrophils for the suppression of the platelet removal. Moreover, a removing material prepared by the method described in the Examples had a thickness of not less than 0.40 mm.

WO 2015/194668 discloses the relationship of the total surface area and the average fiber diameter of the fibrous carrier, with the platelet penetration rate. However, the Examples describe only non-woven fabrics having average fiber diameters of 1.1 to 2.3 μm, and there is no disclosure on the relationship regarding knitted fabrics or woven fabrics having fiber diameters of 10 to 60 μm. Moreover, there is neither disclosure nor suggestion on an idea about the thickness of the material for removing neutrophils for the suppression of the platelet removal.

JP 2008-80114 A describes that the thickness of each sheet of the adsorption carrier is preferably 0.1 mm to 10 cm from the viewpoint of ease of handling. However, there is no description on the removal of platelets, and there is neither disclosure nor suggestion on an idea about the thickness of the material for removing neutrophils for the suppression of the platelet removal. Further, JP 2008-80114 A describes that clogging easily occurs during blood circulation in cases where the bulk density is too high.

It could therefore be helpful to provide a material for removing neutrophils, capable of efficiently removing neutrophils while suppressing removal of platelets.

SUMMARY

We found that, even in cases where the bulk density is increased due to reduction of the thickness of the material, the platelet removal rate can be decreased, and that, by controlling the thickness as well as the porosity within appropriate ranges, neutrophils can be efficiently removed while suppressing removal of platelets.

Disclosed herein is:

(1) A material for removing neutrophils, the material being a knitted fabric or a woven fabric including a fiber having a fiber diameter of 10 to 60 μm, wherein the knitted fabric or the woven fabric has a thickness of 0.10 to 0.40 mm and a porosity of 10 to 30%.

(2) The material for removing neutrophils, according to (1), wherein the knitted fabric or the woven fabric has a bulk density of 0.26 to 0.40 g/cm$^3$.

(3) The material for removing neutrophils, according to (1) or (2), wherein the knitted fabric or the woven fabric has an amino group content of 0.3 to 1.2 mmol per 1 g of dry mass.

(4) The material for removing neutrophils, according to any of (1) to (3), wherein the knitted fabric or the woven fabric has an amide group content of 2.0 to 4.0 mmol per 1 g of dry mass.

(5) The material for removing neutrophils, according to any of (1) to (4), wherein the knitted fabric or the woven fabric contains the fiber as a bundle of 30 to 45 filaments.

(6) The material for removing neutrophils, according to any of (1) to (5), wherein the fiber is a sea-island type composite fiber.

(7) The material for removing neutrophils, according to (6), wherein the sea-island type composite fiber contains polystyrene or a polystyrene derivative as a sea component, and polypropylene as an island component.

(8) A column for removing neutrophils including the material for removing neutrophils, according to any of (1) to (7), the material being packed at 0.1 to 0.4 g/cm$^3$.

(9) A method of producing the material for removing neutrophils, according to any of (1) to (8), the method including a step of binding a compound to a knitted fabric or a woven fabric containing a fiber having a fiber diameter of 10 to 60 μm while a tension is applied to the fabric such that an elongation rate of 1 to 20% is achieved in the longitudinal direction and/or transverse direction.

The material for removing neutrophils is capable of removing neutrophils while suppressing removal of platelets contained in blood. Therefore, the material can be used as a carrier for blood treatment such as extracorporeal circulation therapy.

BRIEF DESCRIPTION OF THE DRAWING

The FIGURE is a diagram illustrating opening portions and non-opening portions in a material for removing neutrophils, wherein the material is a knitted fabric.

DESCRIPTION OF SYMBOLS

1 Opening portion of the material for removing neutrophils

2 Non-opening portion (fibers) of the material for removing neutrophils

DETAILED DESCRIPTION

The material for removing neutrophils is characterized in that it is a knitted fabric or a woven fabric comprising a fiber having a fiber diameter of 10 to 60 μm, wherein the knitted fabric or the woven fabric has a thickness of 0.10 to 0.40 mm and a porosity of 10 to 30%.

The term "fiber diameter" means an average value obtained by randomly collecting 10 small sample pieces of fibers forming the knitted fabric or the woven fabric, taking photographs of the sample pieces at a magnification of ×1000 to ×3000 using a scanning electron microscope, measuring the diameters of the fibers at 10 positions per photograph (a total of 100 positions), and then averaging the measured values.

The material for removing neutrophils has a fiber diameter of 10 to 60 μm, preferably 15 to 40 μm, from the viewpoint of increasing the contact area, maintaining the strength of the material, and suppressing the removal of the platelets.

The term "filament" means a fiber with a continuous length. From the viewpoint of improving the ease of handling and the removal performance, the fiber used for the material for removing neutrophils is preferably a multifilament composed of a plurality of monofilaments bundled together. The number of filaments in the multifilament is preferably 5 to 100, more preferably 15 to 50, still more preferably 30 to 45. Any preferred lower limit can be combined with any preferred upper limit.

The material for removing neutrophils needs to be a knitted fabric or a woven fabric since a knitted fabric or a woven fabric has a high packing mass per unit volume, has uniform channels, and can be easily packed into a container such as a column for removing neutrophils.

The term "knitted fabric" means a sheet-like structure prepared by knitting fibers. Examples of a method of forming the knitted fabric include weft knitting (flat knitting, rib knitting, or pearl knitting) and warp knitting (single tricot knitting, single cord knitting, or single atlas knitting). In particular, from the viewpoint of forming an opening portion shape suitable for penetration of blood cells, weft knitting is preferred.

The term "woven fabric" means a sheet-like structure prepared by weaving fibers. Examples of a method of forming the woven fabric include plain weaving, twill weaving, satin weaving, dutch weaving, and twill dutch weaving. In particular, from the viewpoint of forming an opening portion shape suitable for penetration of blood cells, plain weaving or twill weaving is preferred.

The fibers constituting the knitted fabric or the woven fabric that is the material for removing neutrophils may be fibers composed of a single component, may be fibers composed of a plurality of components, or may be a mixture of different fibers. The cross-sectional structure of the fibers is not limited. The fibers constituting the knitted fabric or the woven fabric are preferably sea-island type composite fibers since these fibers have high tensile strength.

The term "sea-island type composite fiber" means a fiber having a cross-sectional structure in which island components composed of a certain polymer are scattered in a sea component composed of a polymer that is different from that of the island components. The sea-island type composite fiber also includes a core-sheath type fiber, which contains only one island component.

The term "sea component" means a polymer present on the surface side of the sea-island type composite fiber. The sea component is preferably composed of a thermoplastic resin from the viewpoint of the processability. As the sea component, a single thermoplastic resin composed of one type of thermoplastic resin, or a single thermoplastic resin composed of two or more types of thermoplastic resins completely compatible with each other, may be used. Alternatively, a mixture or the like of two or more types of thermoplastic resins that are incompatible with each other may be used. In particular, the sea component is more preferably composed of a single thermoplastic resin from the viewpoint of allowing uniform adsorption of substances.

The term "thermoplastic resin" means a polymer material that can be plasticized and molded by heat. The thermoplastic resin is not limited as long as it is a thermoplastic polymer. The thermoplastic resin preferably contains a polymer having a repeat structure that contains a functional group reactive with a carbon cation, such as an aryl group or a hydroxy group, and examples of the polymer include polyethylene terephthalate, polybutylene terephthalate, poly (aromatic vinyl compound), polyester, polysulfone, polyether sulfone, polystyrene, polydivinylbenzene, cellulose, cellulose triacetate, polyvinyl pyrrolidone, polyacrylonitrile, sodium polymethallyl sulfonate, and polyvinyl alcohol, and derivatives thereof. In cases of the use in the material for removing neutrophils, the thermoplastic resin more preferably contains poly (aromatic vinyl compound), polyethylene terephthalate, polybutylene terephthalate, polystyrene, polysulfone, polyether sulfone, polydivinylbenzene, cellulose triacetate, polyvinylpyrrolidone, polyacrylonitrile, or sodium polymethallyl sulfonate, or a derivative thereof, which is a polymer having no hydroxy group. In particular, the thermoplastic resin still more preferably contains polystyrene or a polystyrene derivative since it contains a large number of aromatic rings per unit mass, and hence various functional groups and reactive functional groups can be easily introduced thereto by Friedel-Crafts reaction. The above thermoplastic resins may be those that are commercially available, or those produced by a known method.

The term "island component" means a polymer that is different from the sea component, and that is scattered in the sea component when viewed in the direction perpendicular to the fiber axis direction of the sea-island type composite fiber.

The island component is preferably polyolefin from the viewpoint of ensuring the strength of the fiber. As the island component, a single polyolefin may be used, or a mixture or the like of two or more types of polyolefins may be used.

The term "polyolefin" means a polymer synthesized using an olefin or an alkene as a monomer. In particular, from the viewpoint of the strength, polypropylene or polyethylene is preferably used as the island component.

Some embodiments of the sea-island type composite fiber include a sea-island type composite fiber in which the sea component is composed of a single thermoplastic resin, and the island component is composed of polyolefin. In another embodiment of the sea-island type composite fiber, the sea component is composed of polystyrene or a polystyrene derivative, and the island component is composed of polypropylene.

The term "porosity" means, in the material for removing neutrophils, the ratio of the area of the opening portions 1 to the sum of the areas of the opening portions 1 and the non-opening portions 2 as illustrated in the FIGURE. The porosity is a value obtained by processing an image captured using a scanner or an optical microscope. More specifically, the porosity can be calculated by "Measurement of Porosity of Knitted Fabric" as described later.

In cases where the porosity is too low, components in blood are likely to cause clogging, and the platelet removal rate increases, leading to an increase in the pressure. On the other hand, in cases where the porosity is too high, the knitted fabric cannot be easily handled due to its low strength, and the contact area with the liquid to be treated decreases, leading to a decrease in the neutrophil-removing performance. From the above reasons, the porosity of the material for removing neutrophils needs to be 10 to 30%, and is preferably 10 to 25%, more preferably 10 to 20%.

Examples of a method of adjusting the porosity of the material for removing neutrophils include a method in which the density adjustment scale of a knitting machine is controlled as described in WO 2018/047929, and a method in which reaction for introduction of amide groups or amino groups is performed while a tension is applied to the knitted fabric or the woven fabric, to prepare the material for removing neutrophils.

The term "thickness" means the distance from one side of a sheet-like knitted fabric or woven fabric to the other side of the fabric. The thickness of the material for removing neutrophils can be measured using a micrometer or the like.

In cases where the material for removing neutrophils is too thick, the platelet removal rate is high, while in cases where the material is too thin, the material cannot be easily handled due to its low strength. Therefore, the thickness of the material for removing neutrophils needs to be 0.10 to 0.40 mm, and is preferably 0.20 to 0.35 mm, more preferably 0.25 to 0.30 mm. Any preferred lower limit can be combined with any preferred upper limit.

The mechanism by which the removal of platelets can be suppressed by reduction of the thickness of the material for removing neutrophils is not clear. However, it can be assumed that, since adhesion of platelets occurs when they roll on the adhesive surface, the reduction of the thickness allows release of the platelets from the adhesive surface due to shortening of the rolling distance.

The thickness of the material for removing neutrophils can be adjusted by adjusting the density adjustment scale of a knitting machine, or by performing reaction for introduction of amide groups or amino groups while a tension is applied to the knitted fabric or the woven fabric.

The term "bulk density" means a value which represents the amount of fibers packed in the fiber structure, and which is determined by dividing the dry mass of the material for removing neutrophils by the volume calculated from the thickness and the area of the material for removing neutrophils. From the viewpoint of suppressing the occurrence of clogging, and from the viewpoint of maintaining the shape and the removal performance, the bulk density of the material for removing neutrophils is preferably 0.10 to 0.40 g/cm$^3$, more preferably 0.15 to 0.40 g/cm$^3$, still more preferably 0.26 to 0.40 g/cm$^3$, especially preferably 0.26 to 0.35 g/cm$^3$. Any preferred lower limit can be combined with any preferred upper limit. To reduce the platelet removal rate, it is preferred to reduce the thickness of the material for removing neutrophils while a bulk density within the preferred range is achieved.

The bulk density of the material for removing neutrophils can be adjusted by adjusting the density adjustment scale of a knitting machine, or by performing reaction for introduction of amide groups or amino groups while a tension is applied to the knitted fabric or the woven fabric.

In cases where the material for removing neutrophils is used for treatment of an inflammatory disease, inflammatory cytokines are preferably removed together with neutrophils since inflammatory cytokines produced from neutrophils also play important roles in exacerbation of inflammatory diseases.

The term "inflammatory disease" means any disease that causes inflammatory reaction in the body. Examples of the inflammatory diseases that can be treated include systemic lupus erythematosus, malignant rheumatoid arthritis, multiple sclerosis, ulcerative colitis, Crohn's disease, druginduced hepatitis, alcoholic hepatitis, hepatitis A, hepatitis B, hepatitis C, hepatitis D, hepatitis E, sepsis (for example, sepsis derived from gram-negative bacteria, sepsis derived from gram-positive bacteria, culture-negative sepsis, or fungal sepsis), influenza, acute respiratory distress syndrome (ARDS), acute lung injury (ALI), pancreatitis, idiopathic interstitial pneumonia (IPF), inflammatory enteritis (for example, ulcerative colitis or Crohn's disease), transfusion of a blood preparation, organ transplantation, reperfusion damage caused by organ transplantation, cholecystitis, cholangitis, and newborn blood group incompatibility.

The term "inflammatory cytokines" means a group of proteins which are produced from various cells such as immunocompetent cells in response to stimuli such as infection and trauma, and which are released extracellularly to exert their actions. Examples of the inflammatory cytokines include interferon-α, interferon-β, interferon-γ, interleukin-1 to interleukin-15, tumor necrosis factor-α, tumor necrosis factor-β, high-mobility group box-1, erythropoietin, and monocyte chemotactic factors.

From the viewpoint of removing inflammatory cytokines, the material for removing neutrophils preferably contains amide groups or amino groups. More preferably, a compound containing an amide group or an amino group is bound to fibers constituting the material for removing neutrophils.

The "amide group" is an amide bond contained in a compound, and the amide bond may be an amide bond of any of a primary amide, a secondary amide, and a tertiary amide. The amide is preferably a secondary amide. Further, at least one amide group contained in the compound is preferably covalently bound to a fiber through an alkylene group. The alkylene group is preferably a methylene group, an ethylene group, a propylene group, or the like. In particular, from the viewpoint of easily introducing amide groups to the fibers, the alkylene group is more preferably a methylene group.

From the viewpoint of imparting an ability to remove inflammatory cytokines, and maintaining the fiber strength, the amide group content per 1 g of dry mass of the material for removing neutrophils is preferably 2.0 to 4.0 mmol, more preferably 2.5 to 3.5 mmol. Any preferred lower limit can be combined with any preferred upper limit.

The amide group content in the material for removing neutrophils can be controlled by the amount of a reagent, or the reaction time, for the introduction of amide groups to the knitted fabric or the woven fabric.

The term "amino group" means a chemical structure containing one or more amines as a partial structure(s). Examples of the amino group include an amino group derived from ammonia, an amino group derived from a primary amine (such as aminomethane, aminoethane, aminopropane, aminobutane, aminopentane, aminohexane, aminoheptane, aminooctane, or aminododecane), an amino group derived from a secondary amine (such as dimethylamine, diethylamine, dipropylamine, phenylethylamine, monomethylaminohexane, or 3-amino-1-propene), an amino group derived from a tertiary amine (such as triethylamine, phenyldiethylamine, or aminodiphenylmethane), and an amino group derived from a compound having a plurality of amino groups (such as ethylenediamine, diethylenetriamine, triethylenetetramine, tetraethylenepentamine, dipropylenetriamine, polyethyleneimine (having a weight average molecular weight of 500 to 100,000), N-methyl-2,2'-diaminodiethylamine, N-acetylethylenediamine, or 1,2-bis (2-aminoethoxyethane); hereinafter referred to as "polyamine").

Among amino groups, amino groups derived from polyamines are suitable for blood treatment since they are highly likely to contact blood components because of their high molecular mobility. On the other hand, in cases where a polyamine has a high molecular weight, steric hindrance of the amino group itself increases, leading to a decrease in the removal performance. Therefore, the number of amino groups in the polyamine is preferably 2 to 7, and the polyamine from which the amino groups are derived is preferably a polyamine having a linear structure as a whole. Examples of a polyamine that satisfies the above conditions include ethylenediamine, diethylenediamine, triethylenediamine, diethylenetriamine, triethylenetriamine, tetraethylenetriamine, triethylenetetramine, tetraethylenetetramine, pentaethylenetetramine, tetraethylenepentamine, pentaethylenepentamine, hexaethylenepentamine, pentaethylenehexamine, hexaethylenehexamine, heptaethylenehexamine, hexaethyleneheptamine, heptaethyleneheptamine, and octaethyleneheptamine. In particular, from the viewpoint of ease of handling, ethylenediamine, diethylenetriamine, triethylenetetramine, tetraethylenepentamine, pentaethylenehexamine, or polyethyleneimine is preferred. Tetraethylenepentamine is more preferred. The amino group is more preferably an amino group derived from a primary amine or a secondary amine.

From the viewpoint of imparting an ability to remove inflammatory cytokines, and increasing the ratio of the neutrophil removal rate to the platelet removal rate, the amino group content per 1.0 g of dry mass of the material for removing neutrophils is preferably 0.3 to 1.2 mmol, more preferably 0.5 to 1.0 mmol. Any preferred lower limit can be combined with any preferred upper limit.

The amino group content in the material for removing neutrophils can be controlled by the amount of a reagent, or the reaction time, for the introduction of amino groups to the knitted fabric or the woven fabric.

Depending on the conditions for the introduction of the amide groups or the amino groups, the knitted fabric or the woven fabric swells, leading to a change in the thickness or the porosity.

The term "dry mass" means the mass of a solid in a dry state. The solid in a dry state means a solid in a state where the amount of the liquid component contained in the solid is not more than 1% by mass. In cases where the mass of a solid is measured, and then the solid is heat-dried at 80° C. at atmospheric pressure for 24 hours, and where the loss of the mass is not more than 1% by mass based on comparison of the mass of the remaining solid with the mass of the undried solid, the solid is regarded as being in a dry state.

The amino group content in the material for removing neutrophils can be measured by carrying out acid-base back titration of amino groups using sodium hydroxide.

The amide group content in the material for removing neutrophils can be measured by hydrolyzing the material for removing neutrophils, to generate amino groups, and then measuring the generated amino groups by carrying out acid-base back titration using sodium hydroxide.

The "material for removing neutrophils" is a material capable of separating and removing at least some of the neutrophils from the liquid to be treated, irrespective of whether components other than neutrophils are removed.

Although the neutrophil removal rate of the material for removing neutrophils is not limited, the neutrophil removal rate is preferably not less than 5%. Even in cases where the neutrophil removal rate is low, a necessary amount of neutrophils can be removed by repeatedly passing the liquid to be treated. In cases where the liquid to be treated is repeatedly passed, the platelet removal rate is more preferably lower than the neutrophil removal rate.

For the purpose of maintaining the platelet count within a range in which the homeostatic function can be maintained, or avoiding a pressure increase to enable circulation for a long time, the platelet removal rate is preferably not more than 22%, more preferably not more than 18%, still more preferably not more than 15%.

More preferably, the platelet removal rate is not more than 22%, and at the same time, the ratio of the neutrophil removal rate to the platelet removal rate is not less than 1.0 based on evaluation of the neutrophil removal rate and the platelet removal rate under the same conditions.

The material for removing neutrophils is preferably used as a material to be packed in a column for removing neutrophils.

The term "column for removing neutrophils" means a container provided with an inlet and an outlet, packed with a material for removing neutrophils.

The amount of the material for removing neutrophils to be packed in the column for removing neutrophils is not limited. The amount is preferably 0.1 to 0.4 g/cm$^3$, more preferably 0.2 to 0.3 g/cm$^3$ in terms of the dry mass of the material for removing neutrophils with respect to the container volume. Any preferred lower limit can be combined with any preferred upper limit.

The material for removing neutrophils is preferably packed in a stacked state, in the column for removing neutrophils.

The term "stacking" means layering two or more sheets of the material for removing neutrophils, closely on each other.

Examples of a method of the packing in a stacked state include a method in which a plurality of sheets of the material for removing neutrophils are layered on each other as in an axial flow column, and a method in which the material for removing neutrophils is wound around a pipe or the like on which holes are formed, such as a radial flow column. The method is especially preferably a method in which the material for removing neutrophils is packed by winding, such as in the case of a radial flow column.

In cases where a column for removing neutrophils using the material for removing neutrophils is used as a blood purifier, the column may be used in combination with another medical device or pharmaceuticals.

The term "blood purifier" means an apparatus containing, in at least part thereof, a medical material for the purpose of extracorporeally circulating blood to remove waste products and harmful substances from the blood. Examples of the blood purifier include extracorporeal circulation columns packed with a knitted fabric or a woven fabric.

Examples of a method of evaluating the neutrophil removal rate or the platelet removal rate include a method in which the material for removing neutrophils is packed in a container provided with an inlet and an outlet, and a liquid containing neutrophils and platelets is passed therethrough, followed by calculating the removal rate based on the difference between the concentrations at the inlet and the outlet.

In cases where blood is used as the liquid containing neutrophils and/or platelets, an anticoagulant needs to be added to prevent blood coagulation. Examples of the anticoagulant include heparin (unfractionated heparin, low-molecular-weight heparin, or a heparin derivative), ethylenediaminetetraacetic acid (hereinafter referred to as "EDTA"), sodium citrate, nafamostat mesilate, and argatroban. EDTA and heparin are not suitable for the evaluation of the platelet removal performance since they have platelet-aggregating action. In the evaluation of the platelet removal performance, nafamostat mesilate, which is used as an anticoagulant for extracorporeal circulation, is preferably used.

Examples of a method of measuring the concentration of neutrophils include a method in which a neutrophil detection reagent is reacted with a liquid containing neutrophils, and then a blood cell fraction that has reacted with the reagent is measured. For the measurement, a flow cytometer or a blood cell analyzer can be used.

Examples of a method of measuring the concentration of platelets include a method in which a platelet detection reagent is reacted with a liquid containing platelets, and then a blood cell fraction that has reacted with the reagent is measured. For the measurement, a flow cytometer or a blood cell analyzer can be used.

In cases where the strength of the material for removing neutrophils is insufficient, friction with a liquid during use may cause brittle fracture on the fiber surface, resulting in generation of fine particles derived by detachment of fibers. In particular, in cases of use in extracorporeal circulation, the generated fine particles may enter the body. Therefore, the generation of the fine particles is preferably reduced as much as possible.

The measurement of the fine particles generated from the material for removing neutrophils can be performed with reference to the General Tests, Processes, and Apparatus, 6.07 Insoluble Particulate Matter Test for Injections (Method 1: Light Obscuration Particle Count Test; pp. 1-2) in The Japanese Pharmacopoeia, Fifteenth Edition (Mar. 31, 2006, the Ministry of Health, Labour and Welfare Ministerial Notification No. 285). Specific examples of the method include a method in which a certain area of the material for removing neutrophils is cut out and packed into a cell, and water in the cell is stirred to extract fine particles, followed by counting the number of fine particles obtained by the extraction. Since the acceptability criterion of the number of insoluble fine particles in an injection solution is not more than 25 particles per 1 mL regarding particles having a particle size of not less than 10 μm, the number of fine particles generated from the material for removing neutrophils is preferably less than 10, more preferably less than 5, in terms of the number of particles having a particle size of not less than 10 μm contained per 1 mL of water used for extraction of 0.01 cm$^3$ of the material.

The amount of the fine particles generated can be controlled by performing reaction for introduction of amide groups or amino groups while a tension is applied to the knitted fabric or the woven fabric. This is assumed to be due to the fact that, by performing the reaction for introduction of amide groups or amino groups while a tension is applied to the knitted fabric or the woven fabric, swelling and shrinking of the knitted fabric or the woven fabric during the introduction reaction can be suppressed, resulting in suppression of destruction of the fiber surface.

Thus, the method of producing the material for removing neutrophils preferably comprises a step of binding a compound to a knitted fabric or a woven fabric containing a fiber having a fiber diameter of 10 to 60 μm while a tension is applied to the fabric such that an elongation rate of 1 to 20% is achieved in the longitudinal direction and/or transverse direction. By the inclusion of the step of binding a compound while a tension is applied, swelling and shrinking of the knitted fabric or the woven fabric that occur during the binding of the compound can be suppressed. Therefore, the thickness and the porosity of the knitted fabric or the woven fabric, the amount of the fine particles generated therefrom, and the like can be adjusted within preferred ranges.

In view of the above, the elongation rate in the longitudinal direction and/or transverse direction of the fabric in the step of binding a compound is preferably 1 to 20%, more preferably 3 to 10%.

The "elongation rate" is the ratio of the difference between the length of the knitted fabric or the woven fabric after the application of the tension and the length of the knitted fabric or the woven fabric before the application of the tension, to the length of the knitted fabric or the woven fabric before the application of the tension.

EXAMPLES

The material for removing neutrophils is described concretely by way of Examples below, but this disclosure is not limited by these examples. Unless otherwise specified, the mass of the knitted fabric or the material for removing neutrophils is dry mass. The fineness means the weight (in grams) per 10,000 m of a fiber, and is represented as dtex. The pH measurement in the acid-base titration was carried out by immersing the electrode of the bench-top PH meter F-74BW (manufactured by HORIBA, Ltd.; provided with a Standard ToupH electrode 9615S-10D) in a solution at 25° C. Before the measurement, calibration was performed using a neutral phosphate standard solution (aqueous monopotassium phosphate solution (3.40 g/L), manufactured by Wako Pure Chemical Industries, Ltd.) and a phthalate standard solution (aqueous potassium hydrogen phthalate solution (10.21 g/L), manufactured by Wako Pure Chemical Industries, Ltd.). The absorbance was measured at room temperature using a UV-visible spectrophotometer (manufactured by Shimadzu Corporation, UV-1280). Before the measurement of the absorbance, blank measurement was carried out for subtraction of the background peak.

Preparation of Knitted Fabric A

Using the following components, Fiber A was obtained as a bundle of 18 filaments of sea-island type composite fibers with 16 islands per filament (fineness: 9 dtex, fiber diameter: 30 μm), under yarn-making conditions at a spinning rate of 1200 m/min.

Island component: polypropylene

Sea component: polystyrene

Composite ratio (mass ratio); island component: sea component=50:50

Using a circular knitting machine (machine name: Circular Knitting Machine MR-1, manufactured by Maruzen Sangyo Co., Ltd.) in which the density adjustment scale was adjusted to 2.5, Fiber A was subjected to weft knitting, to prepare Knitted Fabric A (thickness: 0.25 mm; porosity: 31%).

Preparation of Knitted Fabric B

Using the same components as those of Fiber A, Fiber B was obtained as a bundle of 36 filaments of sea-island type composite fibers with 704 islands per filament (fineness: 3 dtex, fiber diameter: 20 μm), under yarn-making conditions at a spinning rate of 1250 m/min. The same operation as in the preparation of Knitted Fabric A was carried out except that Fiber B was used, to prepare Knitted Fabric B (thickness: 0.20 mm, porosity: 35%).

Preparation of Knitted Fabric C

Using the same components as those of Fiber A, Fiber C was obtained as a bundle of 36 filaments of 256 sea-island type composite fibers per filament (fineness: 3 dtex, fiber diameter: 20 μm), under yarn-making conditions at a spinning rate of 1250 m/min. The same operation as in the preparation of Knitted Fabric A was carried out except that Fiber C was used, to prepare Knitted Fabric C (thickness: 0.20 mm, porosity: 35%).

Preparation of Knitted Fabric D

The same operation as in the preparation of Knitted Fabric A was carried out except that the Fiber C obtained was used, and that the density adjustment scale of the circular knitting machine was set to 2.0, to prepare Knitted Fabric D (thickness: 0.22 mm, porosity: 31%).

Preparation of Knitted Fabric E

The same operation as in the case of Knitted Fabric A was carried out except that Fiber B was used, and that the density adjustment scale of the circular knitting machine was adjusted to 3.5, to prepare Knitted Fabric E (thickness: 0.18 mm, porosity: 45%).

Preparation of Knitted Fabric F

Using the following components, a 16-island sea-island type composite fiber (fineness: 160 dtex, fiber diameter: 20 μm; hereinafter referred to as "Fiber D") described in WO 2018/047929 was obtained.

Island component: polypropylene

Sea component (mass ratio); polystyrene: polypropylene=92:8

Composite ratio (mass ratio); island component: sea component =50:50

The same operation as in the case of Knitted Fabric A was carried out except that Fiber D was used, and that the density adjustment scale of the circular knitting machine was adjusted to 3.5, to prepare Knitted Fabric F (thickness: 0.22 mm, porosity: 48%).

Comparative Example 1

Three grams of Knitted Fabric A was immersed in a mixed solution composed of 6 g of N-methylol-α-chloroacetamide (hereinafter referred to as "NMCA"), 85 g of nitrobenzene, 85 g of 98% by mass sulfuric acid, and 86 mg of paraformaldehyde (hereinafter referred to as "PFA"), and then the reaction was allowed to proceed at 20° C. for 1 hour. The fibers after the reaction were washed with nitrobenzene, and then the reaction was stopped with methanol, followed by further washing the fibers with methanol, to obtain chloroacetamidomethyl-modified Knitted Fabric A.

To the chloroacetamidomethyl-modified Knitted Fabric A, 0.85 g of tetraethylenepentamine (hereinafter referred to as "TEPA") was added, and the reaction was allowed to proceed at 30° C. for 3 hours. Subsequently, the fibers were washed with 200 mL of dimethyl sulfoxide (hereinafter referred to as "DMSO") on a glass filter. Thereafter, the fibers were added into 170 mL of a solution of 0.4 g of 4-chlorophenyl isocyanate in DMSO, and the reaction was allowed to proceed at 30° C. for 1 hour, followed by washing the fibers with 200 mL of each of DMSO and distilled water on a glass filter, to obtain a material for removing neutrophils of Comparative Example 1.

Comparative Example 2

According to description in JP 2019-136499 A, a reaction liquid (hereinafter referred to as "NMCA modification reaction liquid") was prepared by mixing, stirring, and dissolving 46% by mass nitrobenzene, 46% by mass sulfuric acid, 1% by mass PFA, and 7% by mass NMCA together at not more than 10° C. After cooling 40 mL of the NMCA modification reaction solution to 5° C., 1 g of Knitted Fabric B was immersed therein, and the reaction was allowed to proceed for 2 hours while the reaction liquid was kept at 5° C. Thereafter, the Knitted Fabric B was removed from the reaction liquid, and then immersed and washed in 40 mL of nitrobenzene. Subsequently, the Knitted Fabric B was removed therefrom, and immersed and washed in methanol, to obtain chloroacetamidomethyl-modified Knitted Fabric B.

In 500 mL of a solution prepared by dissolving TEPA to a concentration of 3 mmol/L, and triethylamine to a concentration of 474 mmol/L in DMSO, 10 g of the chloroacetamidomethyl-modified Knitted Fabric B was immersed, and the reaction was allowed to proceed for 3 hours at 40° C. Thereafter, the Knitted Fabric B after the reaction was removed from the reaction liquid, immersed and washed in 500 mL of DMSO, immersed and washed in 500 mL of methanol, and then immersed and washed in 500 mL of water, to obtain a material for removing neutrophils of Comparative Example 2.

Comparative Example 3

The same operation as in Comparative Example 2 was carried out except that a piece of 6 cm×6 cm was cut out from Knitted Fabric C placed in a flat state, that the four sides of the piece were fixed to a stainless steel jig to keep the size of 6 cm×6 cm, and that the piece was immersed in the NMCA modification reaction liquid together with the jig, to obtain a material for removing neutrophils of Comparative Example 3.

Example 1

The same operation as in Comparative Example 2 was carried out except that a piece of 6 cm×6 cm was cut out from Knitted Fabric C placed in a flat state, that the four sides of the piece were fixed to a stainless steel jig while a tension was applied to expand the piece to a size of 7 cm×7 cm, and that the piece was immersed in the NMCA modification reaction liquid together with the jig, to obtain a material for removing neutrophils of Example 1.

Example 2

The same operation as in Example 1 was carried out except that the four sides of the cut piece of Knitted Fabric C were fixed to a stainless steel jig while a tension was applied such that the piece was expanded to have a size of 6.5 cm (length)×6.0 cm (width), to obtain a material for removing neutrophils of Example 2.

Example 3

The same operation as in Example 1 was carried out except that the four sides of the cut piece of Knitted Fabric C were fixed to a stainless steel jig while a tension was applied such that the piece was expanded to have a size of 6.0 cm (length)×6.5 cm (width), to obtain a material for removing neutrophils of Example 3.

Example 4

The same operation as in Example 1 was carried out except that the four sides of the cut piece of Knitted Fabric C were fixed to a stainless steel jig while a tension was applied such that the piece was expanded to have a size of 6.3 cm (length)×6.3 cm (width), to obtain a material for removing neutrophils of Example 3.

Example 5

The same operation as in Example 1 was carried out except that the concentration of TEPA was 0.5 mmol/L, to obtain a material for removing neutrophils of Example 5.

Example 6

The same operation as in Example 1 was carried out except that the concentration of TEPA was 1 mmol/L, to obtain a material for removing neutrophils of Example 6.

Example 7

The same operation as in Example 1 was carried out except that the concentration of TEPA was 4 mmol/L, to obtain a material for removing neutrophils of Example 7.

Example 8

The same operation as in Example 1 was carried out except that the concentration of TEPA was 0 mmol/L, to obtain a material for removing neutrophils of Example 8.

Example 9

The same operation as in Example 1 was carried out except that the concentration of NMCA was 0% by mass, and that the concentration of TEPA was 0 mmol/L, to obtain a material for removing neutrophils of Example 9.

Example 10

The same operation as in Comparative Example 2 was carried out except that Knitted Fabric E was used, to obtain a material for removing neutrophils of Example 10.

Comparative Example 4

The same operation as in Comparative Example 2 was carried out except that Knitted Fabric D was used, to obtain a material for removing neutrophils of Comparative Example 4.

Comparative Example 5

NMCA in an amount of 4.6 g was added to a mixed solution of 31 g of nitrobenzene and 31 g of 98% by mass sulfuric acid, and the resulting mixture was stirred at 10° C. to dissolve the NMCA, to provide an NMCA solution. Subsequently, 0.2 g of PFA was added to 2.0 g of nitrobenzene and 2.0 g of 98% by mass sulfuric acid, and the resulting mixture was stirred at 20° C. to dissolve the PFA, to provide a PFA solution. After cooling 4.2 g of the PFA solution to 5° C., 64.3 g of the NMCA solution was mixed therewith, and the resulting solution was stirred for 5 minutes, followed by adding 1 g of Knitted Fabric F thereto, and allowing the reaction to proceed at 5° C. for 4 hours. The Knitted Fabric F after the reaction was immersed in 200 ml of nitrobenzene at 0° C. to stop the reaction, and nitrobenzene adhering to the knitted fabric was washed away with methanol.

After dissolving 0.41 g of TEPA and 2.1 g of triethylamine in 51 g of DMSO, the Knitted Fabric F after the washing with methanol was added to the resulting solution, and the reaction was allowed to proceed at 40° C. for 3 hours. The knitted fabric was collected on a glass filter by filtration, and washed with 500 mL of DMSO, 3 L of distilled water, and physiological saline, to obtain a material for removing neutrophils of Comparative Example 5.

Measurement of Thickness of Knitted Fabric

The thickness of the material for removing neutrophils was measured at five random sites using a micrometer (manufactured by Mitutoyo Corporation) at a measuring force of 2.5 N, and the average of the measured values was calculated to determine the thickness (mm). In cases where the thickness of the material for removing neutrophils was not more than 0.5 mm, a stack of four sheets of the material for removing neutrophils was subjected to the measurement, and the measured value was divided by the number of the sheets stacked, to perform the calculation. The thickness of the knitted fabric was rounded to two decimal places.

Measurement of Porosity of Knitted Fabric

A piece with a size of 3 cm×3 cm was cut out from the material for removing neutrophils, and immersed in water contained in a transparent bag. The bag was sealed after removal of air bubbles, and then imaging was performed using a scanner (manufactured by EPSON; GT-X980) and driver software (EPSON Scan) in which the "manuscript type" was set to "reflecting original"; the "automatic exposure" was set to "for photographs"; the "resolution" was set to 2400 dpi; the "image type" was set to 16-bit gray; and all "adjustments" were set to "off". The captured image was analyzed by image processing software ("Photoshop Elements 14", manufactured by Adobe Systems). In this process, the entire material for removing neutrophils was cut out such that edge portions of the material for removing neutrophils were not included. Image adjustment was carried out by setting the "brightening of shadows" and the "halftone contrast" to 100% in the "shadow/highlight", and then setting the "contrast" to 100 and the "brightness" to 10 in the "brightness/contrast", to correct the opening portions 1 in the material for removing neutrophils and the non-opening portions 2 in the material for removing neutrophils on the image. In cases where some of the opening portion and/or the non-opening portions could not be corrected, the opening portions were painted black, and the non-opening portions were painted white using the brush tool for drawing. Binarization was performed by conversion into a two-tone image using color correction by a filter. After opening the histogram of the window, the ratio of the area of the black part to the total area of the analyzed image was obtained to determine the porosity (%). The measurement was carried out in the same manner for five different sheets of the material for removing neutrophils, and the average was calculated. The porosity was rounded to the nearest integer.

Measurement of Bulk Density of Knitted Fabric

The material for removing neutrophils, in an amount corresponding to 37 $cm^2$, was cut into disks having a diameter of 28 mm, and 20 mL of 6 mol/L aqueous sodium hydroxide solution was added thereto, followed by stirring the resulting mixture for 30 minutes, and separating the material for removing neutrophils, by filtration using a filter paper. Subsequently, the material for removing neutrophils, separated by the filtration was added to 20 mL of ion-exchanged water, and the resulting mixture was stirred for 30 minutes, followed by separating the material by filtration using a filter paper. The addition of the material for removing neutrophils to ion-exchanged water and the separation of the material by filtration were repeated until the pH of the ion-exchanged water to which the material was added became 7, to obtain a desalted material for removing neutrophils. The desalted material for removing neutrophils was left to stand for 48 hours under conditions at 80° C. at normal pressure, and then the mass of the material was measured. The dry mass of the neutrophil material was divided by the volume (the product of the cut-out area and the thickness), to calculate the bulk density ($g/cm^3$). The bulk density was rounded to two decimal places.

Measurement of Amino Group Content

The amino group content in the material for removing neutrophils was calculated by performing acid-base back titration of the amino groups in the material for removing neutrophils. To a 200-mL round-bottomed flask, 1.5 g of the material for removing neutrophils was added, and the flask was left to stand at 80° C. for 48 hours in a dryer, to obtain a dried material for removing neutrophils. Subsequently, 1.0 g of the dried material for removing neutrophils and 50 mL of 6 mol/L aqueous sodium hydroxide solution were placed in a polypropylene container, and the resulting mixture was stirred for 30 minutes, followed by separating the material for removing neutrophils, by filtration using a filter paper. Subsequently, the material for removing neutrophils, separated by the filtration was added to 50 mL of ion-exchanged water, and the resulting mixture was stirred for 30 minutes, followed by separating the material by filtration using a filter paper. The addition of the material for removing neutrophils to ion-exchanged water and the separation of the material by filtration were repeated until the pH of the ion-exchanged water to which the material was added became 7, to obtain a desalted material for removing neutrophils. After the desalted material for removing neutrophils was left to stand for 48 hours under conditions at 80° C. at normal pressure, 1.0 g of the material for removing neutrophils and 30 mL of 0.1 mol/L hydrochloric acid were placed in a polypropylene container, and the resulting mixture was stirred for 10 minutes. After the stirring, 5 mL of the solution alone was removed and transferred into a polypropylene container. Subsequently, 0.1 mL of 0.1 mol/L aqueous sodium hydroxide solution was added dropwise to the obtained solution. Thereafter, the resulting mixture was stirred for 10 minutes, and the pH of the solution was measured. The dropwise addition followed by 10 minutes of stirring, and the pH measurement, were repeated in the same manner until the pH of the solution exceeded 8.5. The amount of the aqueous sodium hydroxide solution that had been added dropwise by this time was regarded as the titer per 1.0 g of the material for removing neutrophils. Using the titer per 1.0 g of the material for removing neutrophils, and Equation (1), the amino group content per 1.0 g of dry mass of the material for removing neutrophils was calculated.

$$\text{Amino group content (mmol) per 1.0 g of dry mass of material for removing neutrophils} = \{\text{liquid volume (30 mL) of 0.1 mol/L hydrochloric acid added/liquid volume (5 mL) of hydrochloric acid removed}\} \times \text{titer (mL) per 1.0 g of material for removing neutrophilis} \times \text{concentration (0.1 mol/L) of aqueous sodium hydroxide solution} \quad (1)$$

The amino group content was rounded to one decimal place.

Measurement of Amide Group Content

In the calculation of the amide group content in the material for removing neutrophils, the amide groups in the material for removing neutrophils were hydrolyzed to generate amino groups, and then the amount of the generated amino groups was measured by carrying out acid-base back titration. In a 200-mL round-bottomed flask, 1.0 g of the material for removing neutrophils and 100 mL of 6 mol/L hydrochloric acid were placed, and the resulting mixture was refluxed at 130° C. for 24 hours. Thereafter, the material for removing neutrophils was recovered by filtration through a filter paper, to obtain a degraded material for removing neutrophils. Subsequently, the whole amount of the obtained degraded material for removing neutrophils and 50 mL of 6 mol/L aqueous sodium hydroxide solution were placed in a polypropylene container, and the resulting mixture was stirred for 30 minutes, followed by separating the material by filtration using a filter paper. Then, the degraded material for removing neutrophils, separated by the filtration was added to 50 mL of ion-exchanged water, and the resulting mixture was stirred for 30 minutes, followed by separating the material by filtration using a filter paper. The addition of the material for removing neutrophils to ion-exchanged water and the separation of the material by filtration were repeated until the pH of the ion-exchanged water to which the material was added became 7, and then the material was left to stand for 48 hours under conditions at 80° C. at normal pressure. Subsequently, the total amount of the material for removing neutrophils and 60 mL of 0.1 mol/L hydrochloric acid were placed in a polypropylene container, and the resulting mixture was stirred for 10 minutes. Thereafter, 5 mL of the solution alone was removed and transferred into a polypropylene container. To the obtained solution, 0.1 mL of 0.1 mol/L aqueous sodium hydroxide solution was added dropwise. Thereafter, the resulting mixture was stirred for 10 minutes, and the pH of the solution was measured. The dropwise addition followed by 10 minutes of stirring, and the pH measurement, were repeated until the pH of the solution exceeded 8.5. The amount of the aqueous sodium hydroxide solution that had been added dropwise by this time was regarded as the titer per 1.0 g of the material for removing neutrophils. Using the titer per 1.0 g of the material for removing neutrophils, and Equation (2), the amide group content per 1.0 g of dry mass of the material for removing neutrophils was calculated.

$$\text{Amino group content (mmol) per 1.0 g of dry mass of material for removing neutrophils} = \{\text{liquid volume (60 mL) of 0.1 mol/L hydrochloric acid added/liquid volume (5 mL) of hydrochloric acid removed}\} \times \text{titer (mL) per 1.0 g of material for removing neutrophilis} \times \text{concentration (0.1 mol/L) of aqueous sodium hydroxide solution} \quad (2)$$

The amide group content was rounded to one decimal place.

Measurement of Neutrophil Removal Rate and Platelet Removal Rate

Blood was collected from healthy volunteers (nafamostat mesylate concentration: 0.13 mg/mL), and the following measurement was performed. Since the half-life of the anticoagulant nafamostat mesylate is short, it was additionally added to the blood at 0.13 mg/mL 30 minutes after the blood collection. The material for removing neutrophils, in an amount of 0.8 $cm^3$, was cut into disks having a diameter of 1 cm, and the disks were stacked and packed into a cylindrical column (1 cm (inner diameter)×1.2 cm (height); volume, 0.94 $cm^3$; outer diameter, 2 cm; made of polycarbonate) provided with a solution inlet/outlet at the top and the bottom, to prepare a column. Lipopolysaccharide (LPS) was added to the blood to 70 EU/mL, and then the blood was activated by stirring at 65 rpm at 37° C. for 30 minutes. The activated blood was passed through the column at a flow rate of 0.63 mL/min, and blood samples were collected at the inlet and the outlet of the column. The collection of the samples at the column outlet was carried out after passing the blood for 3.5 minutes to 6.5 minutes as measured from Minute 0, the time point when the blood entered the column. Using an Automated Hematology Analyzer (model number: XT-1800i; Sysmex Corporation), the neutrophil count and the platelet count of each obtained sample were measured, and the measured values were used to calculate the neutrophil removal rate according to Equation (3), and the platelet removal rate according to Equation (4). From the values of the neutrophil removal rate and the platelet removal rate, the ratio of (neutrophil removal rate/platelet removal rate) was calculated.

$$\text{Neutrophil removal rate (\%)} = \{(\text{neutrophil count at column inlet}) - (\text{neutrophil count at column outlet}\}/(\text{neutrophil count at column inlet}) \times 100 \quad (3)$$

$$\text{Platelet removal rate (\%)} = \{(\text{platelet count at column inlet}) - (\text{platelet count at column outlet}\}/(\text{neutrophil count at column inlet}) \times 100 \quad (4)$$

The neutrophil removal rate and the platelet removal rate were rounded to the nearest integer.

Measurement of IL-8 Removal Rate

The material for removing neutrophils was cut into disks having a diameter of 6 mm, and two disks were placed in each polypropylene container. A fetal bovine serum was prepared such that the concentration of interleukin 8 (hereinafter referred to as "IL-8"), which is a cytokine, was 2000 pg/mL. The fetal bovine serum was added to the container in an amount of 300 mL per 1 $cm^3$ of the material for removing neutrophils. The resulting mixture was mixed by inversion for 24 hours in an incubator at 37° C., and then subjected to measurement of the IL-8 concentration in the fetal bovine serum by the ELISA method (Human CXCL8/IL-8 Quantikine ELISA Kit; R&D Systems). From the IL-8 concentrations measured before and after the mixing by inversion, the IL-8 removal rate was calculated according to Equation (5).

$$IL-8 \text{ Removal Rate } (\%) = \{IL-8 \text{ concentration } (pg/\text{mL}) \text{ before mixing by inversion} - IL-8 \text{ concentration} (pg/\text{mL}) \text{ after mixing by inversion}\} / IL-8 \text{ concentration } (pg/\text{mL}) \text{ before mixing by inversion} \times 100 \quad (5)$$

The IL-8 removal rate was rounded to the nearest integer.

Table 1 shows the results of measurement of the thickness, the porosity, the bulk density, the amino group and amide group contents, the neutrophil removal rate, the platelet removal rate, the ratio of (neutrophil removal rate/platelet removal rate), and the IL-8 removal rate, of the knitted fabric of each of Examples 1 to 10 and Comparative Examples 1 to 5.

TABLE 1

| | Thickness [mm] | Porosity [%] | Bulk density [g/cm³] | Amino group content per 1.0 g of dry mass [mmol] | Amide group content per 1.0 g of dry mass [mmol] | IL-8 removal rate [%] | Neutrophil removal rate [%] | Platelet removal rate [%] | Neutrophil removal rate/platelet removal rate |
|---|---|---|---|---|---|---|---|---|---|
| Example 1 | 0.25 | 16 | 0.32 | 1.2 | 3.5 | 12 | 13 | 11 | 1.2 |
| Example 2 | 0.30 | 10 | 0.26 | 0.9 | 3.1 | 17 | 19 | 13 | 1.5 |
| Example 3 | 0.35 | 20 | 0.28 | 1.0 | 2.6 | 23 | 18 | 18 | 1.0 |
| Example 4 | 0.39 | 15 | 0.32 | 1.0 | 2.7 | 32 | 20 | 21 | 1.0 |
| Example 5 | 0.25 | 18 | 0.32 | 0.1 | 3.4 | 4 | 9 | 4 | 2.3 |
| Example 6 | 0.25 | 25 | 0.30 | 0.3 | 3.1 | 10 | 9 | 5 | 1.8 |
| Example 7 | 0.24 | 16 | 0.28 | 1.4 | 2.6 | 10 | 5 | 10 | 0.5 |
| Example 8 | 0.25 | 16 | 0.31 | 0.0 | 3.5 | 1 | 10 | 4 | 2.5 |
| Example 9 | 0.25 | 17 | 0.31 | 0.0 | 0.0 | 1 | 8 | 4 | 2.0 |
| Example 10 | 0.36 | 12 | 0.22 | 1.0 | 2.7 | 22 | 14 | 18 | 0.8 |
| Comparative Example 1 | 0.52 | 4 | 0.25 | 1.9 | 3.1 | 23 | 12 | 35 | 0.3 |
| Comparative Example 2 | 0.43 | 7 | 0.21 | 0.8 | 2.4 | 30 | 21 | 30 | 0.7 |
| Comparative Example 3 | 0.41 | 10 | 0.21 | 1.1 | 2.5 | 31 | 20 | 24 | 0.8 |
| Comparative Example 4 | 0.38 | 3 | 0.29 | 1.2 | 2.5 | 38 | 24 | 46 | 0.5 |
| Comparative Example 5 | 0.45 | 13 | 0.25 | 1.5 | 2.4 | 20 | 15 | 25 | 0.6 |

From the results in Table 1, it can be seen that, since the knitted fabric of the material for removing neutrophils has a thickness and a porosity within the specific ranges, the material is capable of removing neutrophils, and excellent in suppression of the platelet removal. It can also be seen that, in cases where the amino group content per 1.0 g of dry mass of the material for removing neutrophils is 0.3 mmol to 1.2 mmol, an excellent cytokine removal performance can be achieved.

Measurement of Amount of Fine Particles Generated

The material for removing neutrophils was cut into a circular shape having a diameter of 26 mm, and placed in a clean container together with 50 mL of ion-exchanged water (hereinafter referred to as "filtered water") that had been passed through a HEPA filter with a pore size of 0.3 μm. The resulting mixture was mixed by 10 times of inversion, and then the liquid was discharged. By this, fiber debris generated from edge faces of the knitted fabric was washed away. This washing operation was repeated once more. The washed knitted fabric was placed on a base plate attached to a stirring-type ultraholder UHP-25K (manufactured by ADVANTEC Co., Ltd.), and an O-ring was placed thereon. The fabric was then sandwiched with a cylindrical container (cell) having a diameter of 18 mm, and fixed with a base mounting bracket. The liquid outlet of the base plate was closed with a silicone tube, and 100 mL/$cm^3$ of the filtered water was added thereto with the knitted fabric being on the bottom side, to confirm the absence of water leakage. A stirring set attached to UHP-25K was installed, and stirring was performed on a magnetic stirrer RCN-7 (manufactured by Tokyo Rika Kikai Co., Ltd.) at a rotation speed of 600 rpm for 5 minutes in a way that the stirring set was not in contact with the knitted fabric. This liquid was collected, and 3 mL of the liquid was measured with a light obscuration automatic particle counter KL-04 (manufactured by Rion Co., Ltd.). The amount of fine particles of not less than 10 μm detected per 1 mL was regarded as the amount of generated fine particles (particles/mL). The results of measurement of the fine particles generated in each of Examples 1 to 3 and Comparative Examples 1 to 3 are shown in Table 2.

TABLE 2

| | Amount of fine particles generated (particles/mL) |
|---|---|
| Example 1 | 2 |
| Example 2 | 4 |
| Example 3 | 3 |
| Comparative Example 1 | 163 |

TABLE 2-continued

| | Amount of fine particles generated (particles/mL) |
|---|---|
| Comparative Example 2 | 15 |
| Comparative Example 3 | 11 |

The results in Table 2 show that the material for removing neutrophils is excellent as a material for use in extracorporeal circulation since the material generates only a small amount of fine particles.

INDUSTRIAL APPLICABILITY

Our material for removing neutrophils can be used especially for removal of neutrophils in the medical field.

What is claimed is:

1. A material that removes neutrophils, the material comprising:

a fabric comprising a fiber having a fiber diameter of 10 to 60 μm, wherein the fabric has a thickness of 0.10 to 0.40 mm measured at a measuring force of 2.5 N, wherein the measuring force of 2.5 N reflects a compressed state of the fabric, and a porosity of 10 to 30%; wherein the fabric is a knitted or a woven fabric; and wherein the material exhibits a platelet removal rate of not more than 22%.

2. The material according to claim 1, wherein the fabric has a bulk density of 0.26 to 0.40 g/cm3.

3. The material according to claim 1, wherein the fabric has an amino group content of 0.3 to 1.2 mmol per 1.0 g of dry mass.

4. The material according to claim 1, wherein the fabric has an amide group content of 2.0 to 4.0 mmol per 1.0 g of dry mass.

5. The material according to claim 1, wherein the fabric contains the fiber as a bundle of 30 to 45 filaments.

6. The material according to claim 1, wherein the fiber is a sea-island type composite fiber.

7. The material according to claim 6, wherein the sea-island type composite fiber contains polystyrene or a polystyrene derivative as a sea component, and polypropylene as an island component.

8. A column that removes neutrophils comprising the material according to claim 1, the material being packed at 0.1 to 0.4 g/cm3.

9. A method of producing the material according to claim 1, the method comprising a step of binding a compound to a fabric containing a fiber having a fiber diameter of 10 to 60 μm while a tension is applied to the fabric such that an elongation rate of 1 to 20% is achieved in a longitudinal direction and/or transverse direction; wherein the fabric is a knitted fabric or a woven fabric.

* * * * *